United States Patent [19]

Booth

[11] 3,952,106
[45] Apr. 20, 1976

[54] ISOCYANOPHENYL CARBAMATES

[75] Inventor: David L. Booth, Crystal Lake, Ill.

[73] Assignee: Morton-Norwich Products, Inc., Chicago, Ill.

[22] Filed: Nov. 11, 1974

[21] Appl. No.: 522,345

Related U.S. Application Data

[62] Division of Ser. No. 277,053, Aug. 1, 1972, Pat. No. 3,862,976.

[52] U.S. Cl................................. 424/300; 424/304
[51] Int. Cl.² ...................... A01N 9/06; A01N 9/20
[58] Field of Search ........................... 424/300, 304; 260/465 D

[56] References Cited
UNITED STATES PATENTS 3,329,702  7/1967  Rohr ............ 260;424/465 D;300 X
3,577,453  5/1971  Rohr ............................... 260/465 D Primary Examiner—Jerome D. Goldberg
Assistant Examiner—A. P. Fagelson
Attorney, Agent, or Firm—Jack Axelrood

[57] ABSTRACT

Novel isocyanophenyl carbamates of the formula

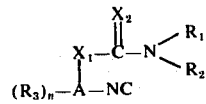

wherein
$X_1$ and $X_2$ are each oxygen or sulfur;
$R_1$ and $R_2$ are each hydrogen, alkyl ($C_1$–$C_4$), aryl, substituted aryl, or cycloaliphatic;
$R_3$ is selected from the group consisting of alkyl ($C_1$–$C_6$), alkoxy, allyl, methylenedioxy, haloalkyl, propargyloxy and allyloxy;
$n$ is an integer from 0 to 4 inclusive; and
A is phenyl or naphthyl.

These compounds are useful as insecticides and acaricides.

10 Claims, No Drawings

ISOCYANOPHENYL CARBAMATES

This is A Division of Ser. No. 277,053, filed Aug. 1, 1972, now U.S. Pat. No. 3,862,976.

BACKGROUND OF THE INVENTION

1. Field of the Invention

This invention relates to novel isocyanophenyl carbamates and their use as insecticides and acaricides.

2. Description of the Prior Art

It is known that bicyclic and tricyclic isonitriles display pesticidal activity (See U.S. Pat. No. 3,419,526); that aliphatic, cycloaliphatic and aralkyl isonitriles containing 12–25 carbon atoms have insecticidal activity (See U.S. Pat. No. 3,012,932); that araliphatic isonitriles having a total of 7–12 carbon atoms exhibit biocidal activity (See British Pat. No. 994,616); and that N-lower alkyl cyanophenyl carbamates have insecticidal properties (See U.S. Pat. No. 3,329,702). However, the present invention provides novel chemical compounds in which both the isocyano (i.e., isonitrilo) and carbamate groups are present in the same molecule, which compounds display insecticidal activity.

SUMMARY OF THE INVENTION

The present invention relates to novel isocyanophenyl carbamates and to the use of these compounds in the control of insects and acarids. The compounds of particular interest are those represented by the formula

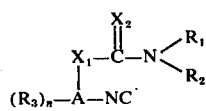

in which $X_1$ and $X_2$ are each oxygen or sulfur;
$R_1$ and $R_2$ are each H, alkyl ($C_1$–$C_4$), aryl, substituted aryl, or cycloaliphatic;
$R_3$ is selected from the group consisting of alkyl ($C_1$–$C_6$), alkoxy, allyl, methylenedioxy, haloalkyl, propargyloxy and allyloxy, and mixtures thereof;
$n$ is an integer from 0 to 4 inclusive; and A is phenyl or naphthyl.

The present invention also provides a method for the control of insect and acarid infestation which comprises applying to the locus of said infestation a pesticidally effective amount of an isocyanophenyl carbamate having the formula:

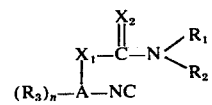

in which $X_1$ and $X_2$ are each oxygen or sulfur;
$R_1$ and $R_2$ are each H, alkyl ($C_1$—$C_4$), aryl, substituted aryl, or cycloaliphatic;
$R_3$ is selected from the group consisting of alkyl ($C_1$—$C_6$), alkoxy, allyl, methylenedioxy, haloalkyl, propargyloxy and allyloxy, and mixtures thereof;
$n$ is an integer from 0 to 4 inclusive; and
A is phenyl or naphthyl.

Illustrative examples of isocyanophenyl carbamates encompassed within the above described genus are:

| Compound No. | Compound | Structure |
|---|---|---|
| 1. | 3-Isocyanophenyl-N-methyl-carbamate | 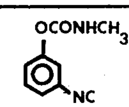 |
| 2. | 3-Isocyanophenyl-N-(4'-bromo-phenyl) carbamate | 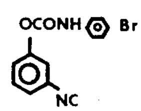 |
| 3. | 3-Isocyanophenyl-N-phenyl-carbamate | 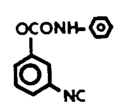 |
| 4. | 4-Isocyanophenyl-N-methyl-carbamate | 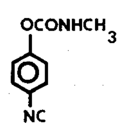 |
| 5. | 5-Isocyano-2-methylphenyl-N-methylcarbamate | 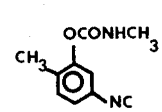 |
| 6. | 3-Isocyanophenyl-N,N-diphenyl-carbamate | 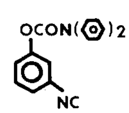 |

-continued

| Compound No. | Compound | Structure |
|---|---|---|
| 7. | 2-Isocyanophenyl-N-methyl-carbamate | 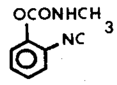 |
| 8. | 3-Isocyanophenyl-N-(n-propyl)-carbamate | 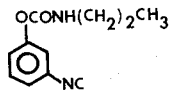 |
| 9. | 3-Isocyanophenyl-N-(n-butyl)-carbamate | 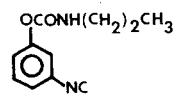 |
| 10. | 3-Isocyanophenyl-N-ethyl-carbamate | 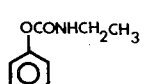 |
| 11. | 3-Isocyanophenyl-N-cyclohexyl-carbamate | 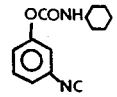 |
| 12. | 2,5-Dimethyl-4-isocyanophenyl-N-methylcarbamate | 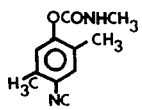 |
| 13. | 4-Isocyanophenyl-N,N-dimethyl-carbamate | 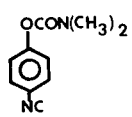 |
| 14. | 4-Isocyano-2-methylphenyl-N-methylcarbamate | 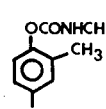 |
| 15. | 2-Isocyanophenyl-N,N-dimethyl-carbamate | 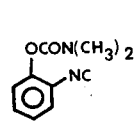 |
| 16. | 3-Isocyanophenyl-N,N-diemthyl-carbamate | 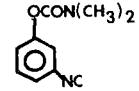 |
| 17. | 4-Isocyano-2-isopropyl-5-methylphenyl-N-methyl-carbamate | 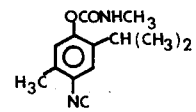 |
| 18. | 4,5-Methylenedioxy-2-isocyanophenyl-N-methyl-carbamate | 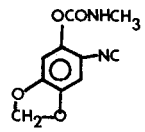 |

-continued

| Compound No. | Compound | Structure |
|---|---|---|
| 19. | 5-Isocyano-1-naphthyl-N-methylcarbamate | 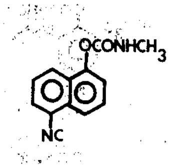 |
| 20. | 2-sec-Butyl-4-isocyano-phenyl-N-methylcarbamate | 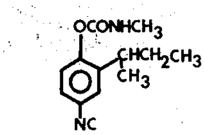 |
| 21. | 3-tert-Butyl-4-isocyano-phenyl-N-methylcarbamate | 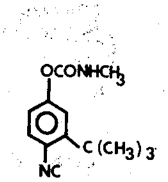 |
| 22. | 3,5-Dimethyl-4-isocyano-phenyl-N-methylcarbamate | 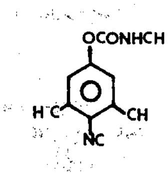 |
| 23. | 2,6-Dimethyl-4-isocyano-phenyl-N-methylcarbamate | 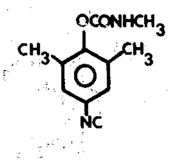 |
| 24. | 2,3-Dimethyl-4-isocyano-phenyl-N-methylcarbamate | 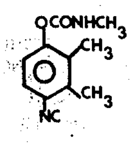 |
| 25. | 4-Isocyano-2-isopropyl-phenyl-N-methylcarbamate | 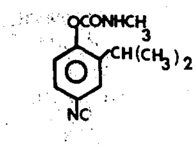 |
| 26. | 3-Isopropyl-5-methyl-4-isocyanophenyl-N-methyl-carbamate | 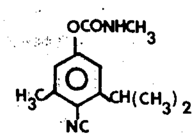 |
| 27. | 3,5-Diisopropyl-4-isocyanophenyl-N-methyl-carbamate | 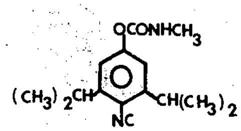 |
| 28. | 2,3,6-Trimethyl-4-isocyano-phenyl-N-methylcarbamate | 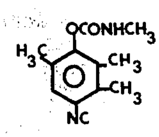 |

| Compound No. | Compound | Structure |
|---|---|---|
| 29. | 2,6-Dimethoxy-4-isocyano-phenyl-N-methylcarbamate | 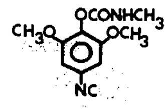 |
| 30. | 2,3,5-Trimethyl-4-isocyanophenyl-N-methylcarbamate | 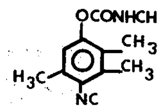 |
| 31. | 2-Isopropoxy-4-isocyanophenyl-N-methylcarbamate | 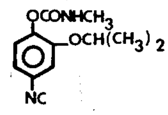 |
| 32. | 3-Isopropoxy-4-isocyanophenyl-N-methylcarbamate | 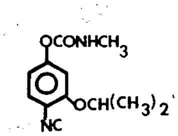 |
| 33. | 4,6-Dimethyl-2-isocyanophenyl-N-methylcarbamate | 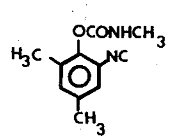 |
| 34. | 4-tert-Butyl-2-isocyanophenyl-N-methylcarbamate | 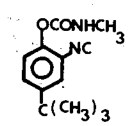 |
| 35. | 4-sec-Butyl-2-isocyanophenyl-N-methylcarbamate | 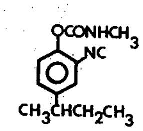 |
| 36. | 4-tert-Pentyl-2-isocyanophenyl-N-methylcarbamate | 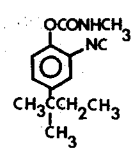 |
| 37. | 3-Methyl-4-isocyanophenyl-N-methylcarbamate | 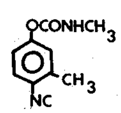 |
| 38. | 4,5-Dimethyl-2-isocyanophenyl-N-methylcarbamate | 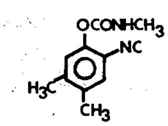 |
| 39. | 4-Isocyanophenyl-N-methyl-dithiocarbamate | 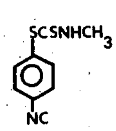 |

-continued

| Compound No. | Compound | Structure |
|---|---|---|
| 40. | 4-Methyl-2-isocyanophenyl-N-methylcarbamate | 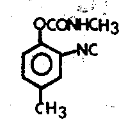 |
| 41. | 4-Isopropyl-2-isocyanophenyl-N-methylcarbamate | 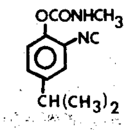 |
| 42. | 4-Ethyl-2-isocyanophenyl-N-methylcarbamate | 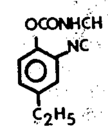 |
| 43. | 2,3,5,6-Tetramethyl-4-isocyanophenyl-N-methylcarbamate | 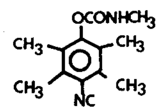 |
| 44. | 2-Allyl-6-methyl-4-isocyanophenyl-N-methylcarbamate | 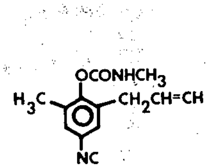 |
| 45. | 3-Trifluoromethyl-4-isocyanophenyl-N-methylcarbamate | 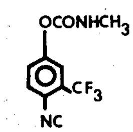 |
| 46. | 2-Propargyloxy-4-isocyanophenyl-N-methylcarbamate | 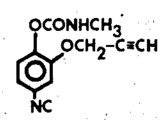 |
| 47. | 2-Allyloxy-4-isocyanophenyl-N-methylcarbamate | 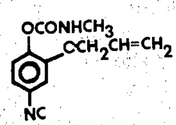 |

As hereinbefore stated, the compounds of the present invention are useful as insecticides and acaricides. They are conveniently applied to the locus of infestation in a variety of ways, for example, as a solution in an organic solvent, as an emulsion, as a spray, on an inert carrier such as clay, kaolin, talc, bentonite, attapulgite, or diatomaceous earth and the like, or as a formulated product in liquid or solid form. Useful organic solvents are the aromatics such as toluene, xylene, benzene, cyclohexane, and alkylated coal tar distillates, aliphatics such as naphthas and petroleum distillates, and various combinations of alcohols, esters, ketones and chlorinated compounds. The present insecticides may be provided as concentrated wettable powders containing as much as 80–90% active ingredient, or as concentrates in solid, liquid, or paste form containing 25–75% by weight of toxicant which may be diluted for application as desired, or as formulated products containing as little as about 5–10% active ingredient.

Illustrative of the preparation of the compounds of the present invention is the following sequence of reactions employed for the synthesis of 4-isocyanophenyl-N-methylcarbamate:

(Reaction I)

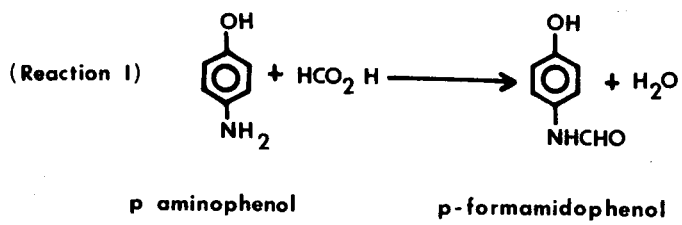

p aminophenol    p-formamidophenol (Reaction II)

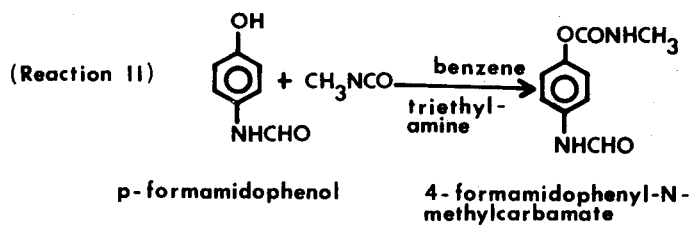

p-formamidophenol    4-formamidophenyl-N-methylcarbamate (Reaction III)

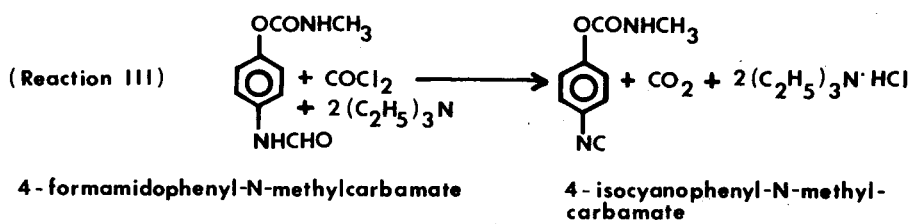

4-formamidophenyl-N-methylcarbamate    4-isocyanophenyl-N-methylcarbamate

Reaction I - Reaction of p-aminophenol with formic acid in aqueous solution

Method A

One mole of p-aminophenol is added to a large excess of 90% formic acid (4–6 moles) and heated at 80°–90°C. for 3 to 4 hours. The reaction mixture is then permitted to cool slowly to room temperature. The resulting p-formamidophenol crystals are filtered off, wash thoroughly with water and then dried. If the product fails to crystallize, it is then poured into an ice-water slurry. The solid is then filtered, washed with water and then dried.

Reaction II - Reaction of p-formamidophenol with methyl isocyanate

Method A

Methyl isocyanate (0.25 mole) is added to a stirred mixture of the formamidophenol (0.20 mole) prepared by Reaction I, benzene or ether (300 ml.), and triethylamine (1 ml.). The reaction mixture is heated at 40°–45°C. for 3–5 hours, then cooled to 12°C. and filtered. If the reaction is not complete, additional methyl isocyanate is added and the reaction continued. The solid 4-formamidophenyl-N-methylcarbamate product is washed with benzene (or ether) and dried.

Reaction III - Reaction of 4-formamidophenyl-N-methylcarbamate with Phosgene

Method A

A solution of phosgene (0.11 mole) in methylene chloride (100 ml.) is added to a refluxing mixture of the formamido carbamate (0.1 mole), methylene chloride (133 ml.) and triethylamine (0.26 mole). Refluxing is continued for an additional ten minutes after the addition is complete. The solvent (methylene chloride) is removed under reduced pressure maintaining the temperature below 50°C. The residue is extracted with benzene and the benzene is removed under reduced pressure leaving the desired 4-isocyanophenyl-N-methylcarbamate.

Reaction I, Method A is not suitable for aminophenols having long chain alkyl substituents, i.e., substituents greater than 4 carbon atoms in length. In the instance where a long chain alkyl aminophenol is employed in the synthesis of an isocyanophenyl carbamate, a preferred method is the following:

Reaction I, Method B

A stirred slurry of the aminophenol (0.2 mole), benzene (200 ml.) and 90% formic acid (0.25 mole) is heated at reflux for 4 hours. The water of reaction and that contained in the formic acid are removed by azeotropic distillation. The dry formamidophenol is now dissolved in benzene for subsequent reaction to form the carbamate.

In the instance where the formamidophenol is prepared according to Reaction I, Method B, then the following procedure is employed to form the formamido carbamate:

Reaction II, Method B

The benzene solution of the formamidophenol is treated with triethylamine until a pH of 9 is obtained. Methyl isocyanate (10% excess or more if necessary) is added and the mixture is heated at 40°–45°C. for 3 to 4 hours, then cooled and filtered. The precipitate of formamidocarbamate is washed with benzene and dried.

An N, N-dialkyl or N,N-diaryl substituted carbamate is prepared from a formamidophenol according to the following equation and method (Reaction II, Method C):

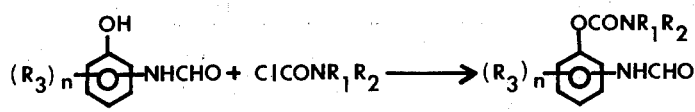

Reaction II, Method C

A dialkyl or diaryl carbamoyl chloride (0.105 mole) is added to a mixture of formamidophenol (0.1 mole), pyridine (0.105 mole) and benzene (150 ml.) and the mixture is stirred for about 1 to 2 hours. If no reaction occurs, acetone is added to effect partial solution and the stirring is continued for 1 to 2 hours. The precipitate of formamidophenyl-N,N-dialkyl or N,N-diaryl carbamate which forms is filtered and dried.

The following are alternate methods which may be employed in the reaction of phosgene with formamidophenyl-N-alkyl carbamates (Reaction III) to form an isocyanophenyl carbamate.

Reaction III, Method B

Phosgene (0.11 mole) is bubbled into a stirred mixture containing the formamidophenyl carbamate (0.10 mole), benzene (250 ml.) and triethylamine (0.28 mole). The temperature is maintained below 15°C. by means of a cooling bath. The cooling bath is removed and the stirring is continued for 1 hour. Water is added and the organic and aqueous layers are separated. The organic layer is dried and evaporated below 50°C. under reduced pressure to provide the desired isocyanophenyl carbamate.

Reaction III, Method C

Phosgene is passed rapidly (1–2 grams/min.) into a homogenized mixture of formamidophenyl carbamate (0.1 mole) in triethylamine (0.26 mole) and methylene chloride (300 ml.). A phosgene excess varying from 10–25% is generally required for complete conversion of amide to isocyano group. The progress of the reaction is followed by using an infra-red spectrophotometer (gradual disappearance of amide band with the simultaneous appearance of the isocyano band at about 2125 cm.$^{-1}$). The reaction must be maintained on the alkaline side. Additional triethylamine may be added if necessary.

The isocyanophenyl carbamate product is isolated by washing the reaction mixture with water, 5% aqueous hydrochloric acid and again with water. The organic layer is separated, dried over anhydrous magnesium sulfate and then concentrated under vacuum below 50°C. Further purification may be accomplished by recrystallizing from benzene, petroleum ether (60°–90°C.) or a combination of both or by chromatography over silica gel.

For a more complete understanding of this invention, reference is now made to the following specific examples illustrating the preparation of the novel compounds of the present invention and their efficacy as insecticides and acaricides.

EXAMPLES 1–15A (Table 1)

The following table, Table 1, summarizes the preparation of representative examples of the present isocyanophenyl carbamates. The Roman numerals and capital letters under the caption "Reactions" refer to the previously described reactions. Thus, for example, a notation IA, IIA, IIIA means Reaction I, Method A, Reaction II, Method A, and Reaction III, Method A.

TABLE 1

| EXAMPLE | COMPOUND NO. | AMINOPHENOL USED | ISOCYANATE | REACTIONS | YIELD* |
|---|---|---|---|---|---|
| 1 | 1 | 3-Aminophenol | Methyl Isocyanate | IA, IIA, IIIA | 67% |
| 2 | 14 | 2-Methyl-4-Aminophenol | " | IA, IIA, IIIB | 84% |
| 3 | 22 | 3,5-Dimethyl-4-Aminophenol | " | IB, IIA, IIIB | 95% |
| 4 | 23 | 2,6-Dimethyl-4-Aminophenol | " | IB, IIA, IIIA | 88% |
| 5 | 25 | 2-Isopropyl-4-Aminophenol | " | IB, IIB, IIIB | 74% |
| 6 | 21 | 3-Tert-Butyl-4-Aminphenol | " | IA, IIA, IIIB | 90% |
| 7 | 16 | 3-Aminophenol | Dimethylcarbamoyl Chloride | IA, IIC, IIIB | 90% |
| 8 | 15 | 2-Aminophenol | " | IA, IIC, IIIB | 91% |
| 9 | 9 | 3-Aminophenol | n-Butylisocyanate | IA, IIA, IIIB | 98% |
| 10 | 8 | 3-Aminophenol | n-Propylisocyanate | IA, IIA, IIIB | 91% |
| 11 | 11 | 3-Aminophenol | Cyclohexylisocyanate | IA, IIA, IIIB | 93% |
| 12 | 19 | 5-Amino-1-Naphthol | Methyl Isocyanate | IA, IIA, IIIC | 75% |
| 13 | 44 | 2-Methyl-6-Allyl-4-Aminophenol | Methyl Isocyanate | IA, IIA, IIIC | 85% |
| 14 | 45 | 3-(Trifluoromethyl)-4-Aminophenol | Methyl Isocyanate | IA, IIA, IIIC | 51% |
| 15 | 46 | 2-Propargyloxy-4-Aminophenol | Methyl Isocyanate | IA, IIA, IIIC | 21% |
| 15A | 47 | 2-Allyloxy-4-Aminophenol | Methyl Isocyanate | IA, IIA, IIIC | 30% |

*Yield of final reaction (i.e. IIIA).

EXAMPLES 16-74

The insecticidal and acaricidal activities of representative and typical isocyanophenyl carbamates of this invention were determined according to the following described methods.

INTRODUCTION

Candidate samples were formulated by dissolving the sample in acetone containing small amounts of emulsifier. The test formulations were then diluted in water to obtain the desired active ingredient concentration. Where solubility was a problem, the diluted test formulation was wet ball-milled.

Southern Armyworm - (*Prodenia eridania*), and Mexican Bean Beetle - (*Epilachna varivestis*).

Lima bean leaves dipped into test solutions of the respective compounds were offered to ten larvae of the Southern armyworm (late third instar) and the Mexican bean beetle (late second instar) for a 48-hour feeding period. Mortality data were recorded. In these tests, as in tests against all other organisms, untreated controls were included for comparative purpose.

Tables 2 and 3 summarize the activity of the indicated isocyanophenyl carbamates against Southern armyworms and Mexican bean beetles respectively. Blank spaces in these and subsequent Tables mean that no tests were conducted at the corresponding particular concentrations.

Table 2

Test Organism: Southern Armyworm (Prodenia eridania)
Percent Mortality
Application Concentration

| Example No. | Compound No. | 0.35% | 0.175% | 0.1% | 0.05% | 0.01% | 0.005% | 0.001% |
|---|---|---|---|---|---|---|---|---|
| 16 | 38 | | | 100 | 0 | | | |
| 17 | 14 | 100 | | 90 | 40 | 20 | | |
| 18 | 12 | 100 | | 100 | 100 | 100 | 10 | |
| 19 | 24 | | | 100 | 100 | 50 | | |
| 20 | 37 | | | 100 | 100 | 100 | 70 | 0 |
| 21 | 30 | | | 100 | 90 | 60 | 0 | |
| 22 | 22 | | | 100 | 100 | 100 | 0 | |
| 23 | 28 | | | 10 | | | | |
| 24 | 25 | | | 90 | 30 | | | |
| 25 | 27 | | | 100 | 100 | 90 | 10 | |
| 26 | 21 | | 100 | 100 | 40 | | | |
| 27 | 17 | 80 | | | | | | |
| 28 | 26 | | | 100 | 100 | 100 | 90 | 0 |
| 29 | 19 | | 90 | 100 | 20 | | | |
| 30 | 4 | 100 | | 100 | 40 | 0 | | |
| 31 | 1 | 40 | | | | | | |
| 32 | 13 | 80 | | | | | | |
| 33 | 15 | 100 | | 0 | | | | |
| 34 | 43 | | | 40 | | | | |
| 35 | 45 | | | 70 | | | | |
| | Untreated | 0 | 0 | 0 | 0 | 0 | 0 | 0 |
| 36 | 23 | | | 30 | | | | |
| 37 | 47 | | | 60 | | | | |

TABLE 3

Test Organism: Mexican Bean Beetle (Epilachna varivestia)
Percent Mortality
Application Concentration

| EXAMPLE NO. | COMPOUND NO. | 1.0% | 0.35% | 0.175% | 0.1% | 0.05% | 0.01% | 0.005% | 0.001% | 0.0005% |
|---|---|---|---|---|---|---|---|---|---|---|
| 38 | 28 | | | | 90 | 50 | | | | |
| 39 | 38 | | | | 100 | 80 | 0 | | | |
| 40 | 14 | | 100 | | 100 | 60 | 20 | | | |
| 41 | 12 | | 100 | | 100 | 100 | 100 | 70 | 0 | |
| 42 | 24 | | | | 100 | 100 | 100 | 0 | | |
| 43 | 37 | | | | 100 | 100 | 100 | 60 | 10 | |
| 44 | 5 | | 100 | | 30 | | | | | |
| 45 | 30 | | | | 100 | 100 | 100 | 50 | 0 | |
| 46 | 22 | | | | 100 | 100 | 100 | 0 | | |
| 47 | 33 | | | | 50 | 0 | | | | |
| 48 | 25 | | | | 100 | 100 | 100 | 0 | | |
| 49 | 27 | | | | 100 | 100 | 100 | 100 | 90 | 40 |
| 50 | 21 | | | 100 | 100 | 100 | 100 | 100 | 30 | |
| 51 | 20 | | | 100 | | | | | | |
| 52 | 17 | | 100 | | 100 | 30 | | | | |
| 53 | 26 | | | | 100 | 100 | 100 | 90 | 50 | |
| 54 | 19 | | | 100 | 100 | 100 | 100 | 70 | 20 | |
| 55 | 11 | | | 20 | | | | | | |
| 56 | 31 | | | | 100 | 100 | 60 | | | |
| 57 | 32 | | | | 100 | 60 | | | | |
| 58 | 29 | | | | 10 | | | | | |
| 59 | 18 | | | | 70 | 0 | | | | |
| 60 | 1 | | 100 | | 100 | 100 | 0 | | | |
| 61 | 4 | | 100 | | 100 | 80 | 50 | | | |
| 62 | 7 | 80 | | | | | | | | |

TABLE 3-continued

| EXAMPLE NO. | COMPOUND NO. | Test Organism: Mexican Bean Beetle (Epilachna varivestia) Percent Mortality Application Concentration | | | | | | | | |
|---|---|---|---|---|---|---|---|---|---|---|
| | | 1.0% | 0.35% | 0.175% | 0.1% | 0.05% | 0.01% | 0.005% | 0.001% | 0.0005% |
| 63 | 15 | | 100 | | 70 | 20 | | | | |
| 64 | 13 | | 80 | | | | | | | |
| 65 | 16 | | 40 | | | | | | | |
| 66 | 42 | | | | 60 | | | | | |
| 67 | 44 | | | | 60 | | | | | |
| 68 | 45 | | | | 100 | | | | | |
| | Untreated | 0 | 0 | 0 | 0 | 0 | 0 | 0 | 0 | 0 |
| 69 | 8 | | | 30 | | | | | | |
| 70 | 10 | | | 10 | | | | | | |
| 71 | 40 | | | | 80 | | | | | |
| 72 | 41 | | | | 20 | | | | | |
| 73 | 36 | 100 | | | | | | | | |
| 74 | 47 | | | | 100 | 80 | 50 | 30 | | |

EXAMPLES 75 – 170

Strawberry Mite — (*Tetranychus atlanticus*)
Excised lima bean plants were infested with 50 to 100 adults of the strawberry spider mite prior to testing. The infested plants were dipped into water dilutions of each test chemical. Treated test plants were allowed to dry and then cultured at room temperature. After 5 days, mortality counts were made. The results are noted in Table 4.

Pea Aphids and Houseflies
Diluted samples were applied to pea aphids and to houseflies in a contact test by means of the Waters vertical spray tower. The spray tower is operated at 10 psi and discharges about 28 ml. of material per minute through a glass atomizer. The spray descends through an 8 inch stainless steel cylinder to the plant or test insects 44 inches below the atomizer.

Pea Aphid — (*Macrosiphum pisi*)
Contact Test

Ten adult pea aphids were sprayed with representative compounds of this invention diluted to the desired concentration and transferred to similarly sprayed pea plants. After a culture period of forty-eight hour, mortality determinations were made. The results are set forth in Table 5.

Systemic Test
To the vermiculite substratum of potted pea seedlings there is applied 25 ml. of the candidate chemical which has been diluted in a suitable non-phytotoxic solvent. Three days after treatment the pea plants are infested with ten adult pea aphids (*Macrosiphum pisi*). Mortality determinations are made after 5 days.

Housefly — (*Musca domestica*)
Fifty adult houseflies were sprayed in a 2 inch high by 5 inch diameter stainless steel cage faced on top and bottom with 14 mesh screen. The insects were retained in the same cages for knockdown observations. The 24-hour mortality of houseflies may be from residual as well as from direct contact. The percentages of knockdown and kill are summarized in Table 6.

TABLE 4

| EXAMPLE NO. | COMPOUND NO. | Test Organism: Strawberry Mite (Tetranychus atlanticus) Percent Mortality Application Concentration | | | | | | | |
|---|---|---|---|---|---|---|---|---|---|
| | | 1.0% | 0.35% | 0.175% | 0.1% | 0.05% | 0.01% | 0.005% | 0.001% |
| 75 | 28 | | | | 100 | 86 | 0 | | |
| 76 | 38 | | | | 100 | 71 | 26 | | |
| 77 | 14 | | 100 | | 0 | | | | |
| 78 | 12 | | | 100 | 100 | 100 | 0 | | |
| 79 | 37 | | | | 90 | 69 | 6 | | |
| 80 | 30 | | | | 100 | 100 | 94 | 73 | 0 |
| 81 | 22 | | | | 100 | 100 | 33 | | |
| 82 | 24 | | | | 86 | | | | |
| 83 | 5 | | 61 | | | | | | |
| 84 | 25 | | | | 100 | 93 | 21 | | |
| 85 | 17 | | 100 | | 0 | | | | |
| 86 | 21 | | | 85 | | | | | |
| 87 | 35 | | | | 25 | | | | |
| 88 | 34 | | | | 41 | | | | |
| 89 | 26 | | | | 100 | 100 | 100 | 95 | 33 |
| 90 | 19 | | | 40 | | | | | |
| 91 | 6 | | 22 | | | | | | |
| 92 | 11 | | | 85 | | | | | |
| 93 | 18 | | | | 53 | | | | |
| 94 | 1 | | 95 | | 83 | 17 | | | |
| 95 | 4 | | 100 | | 100 | 100 | 0 | | |
| 96 | 7 | | 47 | | | | | | |
| 97 | 13 | | 100 | | 19 | | | | |
| 98 | 15 | | 95 | | 0 | | | | |
| 99 | 16 | | 52 | | | | | | |

TABLE 4-continued

Test Organism: Strawberry Mite (Tetranychus atlanticus)
Percent Mortality
Application Concentration

| EXAMPLE NO. | COMPOUND NO. | 1.0% | 0.35% | 0.175% | 0.1% | 0.05% | 0.01% | 0.005% | 0.001% |
|---|---|---|---|---|---|---|---|---|---|
| 100 | 42 | | | | 95 | | | | |
| 101 | 44 | | | | 100 | | | | |
| 102 | 8 | | | 21 | | | | | |
| | Untreated | 0 | 0 | 0 | 0 | 0 | 0 | 0 | 0 |
| 103 | 9 | | | | 71 | | | | |
| 104 | 10 | | | | 83 | | | | |
| 105 | 40 | | | | 78 | 58 | 13 | | |
| 106 | 41 | | | | 53 | 37 | 0 | | |
| 107 | 2 | 100 | | | 0 | | | | |
| 108 | 3 | 79 | | | 0 | | | | |
| 109 | 36 | 100 | | | 0 | | | | |
| 110 | 39 | 51 | | | 0 | | | | |
| 111 | 46 | | | | 15 | | | | |

TABLE 5

Test Organism: Pea Aphids (Macrosiphum pisi)
CONTACT TEST
Percent Mortality
Application Concentration

| EXAMPLE NO. | COMPOUND NO. | 1.0% | 0.35% | 0.175% | 0.1% | 0.05% | 0.01% | 0.005% | 0.001% |
|---|---|---|---|---|---|---|---|---|---|
| 112 | 33 | | | | 90 | 0 | | | |
| 113 | 38 | | | | 100 | 80 | 20 | | |
| 114 | 14 | | 100 | | 20 | | | | |
| 115 | 12 | | 100 | | 100 | 100 | 80 | 75 | 10 |
| 116 | 24 | | | | 100 | 100 | 100 | 0 | |
| 117 | 37 | | | | 100 | 50 | 20 | | |
| 118 | 5 | | 100 | | 80 | 50 | | | |
| 119 | 30 | | | | 100 | 90 | 80 | 20 | |
| 120 | 22 | | | | 100 | 100 | 90 | 0 | |
| 121 | 28 | | | | 10 | | | | |
| 122 | 25 | | | | 100 | 100 | 100 | 0 | |
| 123 | 27 | | | | 10 | | | | |
| 124 | 21 | | | 100 | 60 | 0 | | | |
| 125 | 20 | | | 90 | | | | | |
| 126 | 17 | | 100 | | 100 | 100 | 0 | | |
| 127 | 34 | | | | 30 | | | | |
| 128 | 26 | | | | 100 | 100 | 0 | | |
| 129 | 19 | | | 100 | 100 | 100 | 60 | 0 | |
| 130 | 31 | | | | 100 | 80 | 50 | | |
| 131 | 32 | | | | 20 | | | | |
| 132 | 18 | | | | 60 | 10 | | | |
| 133 | 1 | | 100 | | 100 | 40 | | | |
| 134 | 4 | | 100 | | 100 | 90 | 0 | | |
| 135 | 7 | | 100 | | 100 | 100 | 23 | | |
| 136 | 13 | | 100 | | 100 | 80 | 30 | | |
| 137 | 15 | | 100 | | 100 | 90 | 10 | | |
| 138 | 16 | | 100 | | 100 | 60 | 0 | | |
| 139 | 42 | | | | 50 | | | | |
| 140 | 43 | | | | 10 | | | | |
| 141 | 44 | | | | 40 | | | | |
| | Untreated | 0 | 0 | 0 | 0 | 0 | 0 | 0 | 0 |
| 142 | 10 | | | 40 | | | | | |
| 143 | 23 | | | | 60 | | | | |
| 144 | 40 | | | | 100 | 90 | 10 | | |
| 145 | 41 | | | | 100 | 60 | 20 | | |
| 146 | 36 | | 100 | | 0 | | | | |
| 147 | 46 | | | | 10 | | | | |
| 148 | 47 | | | | 20 | | | | |
| | | | | | SYSTEMIC TEST | | | | | |
| 149 | 24 | | | | 100 | 80 | 50 | | |
| 150 | 20 | | | | 90 | 40 | | | |
| 151 | 4 | | 100 | | 0 | | | | |
| 152 | 7 | | | 30 | | | | | |
| 153 | 40 | | | | 20 | | | | |
| 154 | 41 | | | | 20 | | | | |

TABLE 6

Test Organism: Housefly (Musca domestica)
Percent Mortality
Application Concentration

| EXAMPLE NO. | COMPOUND NO. | 0.35% KD[a] | Kill[b] | 0.175% KD[a] | Kill[b] | 0.1% KD[a] | Kill[b] | 0.05% KD[a] | Kill[b] | 0.01% KD[a] | Kill[b] |
|---|---|---|---|---|---|---|---|---|---|---|---|
| 155 | 12 | 100 | 100 | | | 20 | 100 | 14 | 98 | 0 | 28 |
| 156 | 14 | 8 | 90 | | | 16 | 62 | 0 | 2 | | |
| 157 | 30 | | | | | 40 | 96 | 0 | 20 | | |
| 158 | 22 | | | | | 20 | 98 | 70 | 88 | 0 | 0 |

TABLE 6-continued

Test Organism: Housefly (Musca domestica)
Percent Mortality
Application Concentration

| EXAMPLE NO. | COMPOUND NO. | 0.35% KD[a] | Kill[b] | 0.175% KD[a] | Kill[b] | 0.1% KD[a] | Kill[b] | 0.05% KD[a] | Kill[b] | 0.01% KD[a] | Kill[b] |
|---|---|---|---|---|---|---|---|---|---|---|---|
| 159 | 38 | 0 | 10 | | | | | | | | |
| 160 | 5 | 14 | 80 | | | | | | | | |
| 161 | 24 | | | | | 0 | 14 | | | | |
| 162 | 37 | | | | | 0 | 30 | | | | |
| 163 | 25 | | | | | 8 | 50 | | | | |
| 164 | 27 | | | | | 30 | 28 | | | | |
| 165 | 21 | | | 76 | 88 | | | | | | |
| 166 | 17 | 100 | 100 | | | 84 | 100 | 0 | 14 | | |
| 167 | 26 | | | | | 100 | 80 | 100 | 76 | 0 | 2 |
| 168 | 19 | | | 22 | 60 | | | | | | |
| 169 | 31 | | | | | 100 | 100 | 92 | 82 | 4 | 8 |
| 170 | 32 | | | | | 0 | 4 | | | | |
| 171 | 7 | 100 | 100 | | | 2 | 2 | 4 | 18 | | |
| 172 | 1 | 0 | 68 | | | | | | | | |
| 173 | 15 | 100 | 100 | | | 22 | 84 | 0 | 4 | | |
| 174 | 16 | 100 | 100 | | | 26 | 70 | 0 | 2 | | |
| 175 | 13 | 24 | 96 | | | 2 | 16 | | | | |
| | Untreated | 0 | 0 | 0 | 0 | 0 | 0 | 0 | 0 | 0 | 0 |
| 176 | 46 | | | | | 0 | 24 | | | | |

[a]Percent of flies knocked down 2 hrs. after treatment application.
[b]Percent of flies killed 24 hrs. after treatment application.

EXAMPLE 177

The systemic insecticidal properties of representative isocyanophenyl carbamates of the present invention were determined according to the following procedure utilizing cucumber seedlings infested with melon aphids.

Cucumber seeds (variety - Chicago Pickling) were planted in 16 oz. plastic pots filled with potting soil and cultured in the greenhouse to the two true leaf growth stage. Cucumber plants previously infested with melon aphids (Aphis gossypii) were introduced into the seedling propagation, whereupon, aphid infestation of the propagation was allowed to progress naturally until approximately 200 aphids per seedling were observed. Test treatments were applied at that time.

Each test compound was applied as a soil drench at rates of 12.5 ppm and 25.0 ppm based on the weight of air dry soil in each replicate. Saran film was used to seal the soil surface of each pot to exclude compound vapors, if any, from insect infested leaf surfaces. Treatments were replicated five times.

The treated cucumber seedlings were cultured at 68°F. under artificial light until final insect counts were made. Live aphid counts were conducted on thirteen sixteenths inch diameter leaf discs removed from the first true leaf of each plant. The following Table sets forth the results obtained:

| | Average No. of Aphids/Leaf Disc Application Concentration[a] | | | |
|---|---|---|---|---|
| | 12.5 ppm | | 25.0 ppm | |
| COMPOUND NO. | Average Insect Count | Percent Mortality[b] | Average Insect Count | Percent Mortality[b] |
| 12 | 0.4 | 99.2 | 0.75 | 99.2 |
| 24 | 0 | 100 | 0 | 100 |
| 26 | 3.5 | 93.1 | 8.0 | 91.9 |
| 30 | 1.25 | 97.5 | 5.0 | 94.9 |
| 37 | 8.5 | 83.1 | 3.25 | 96.7 |
| Control | 50.5 | | 98.2 | |

[a]Based on the weight of air dry soil used in each replicate.
[b]Calculated as $\frac{(Control-Actual)}{Control} \times 100$

EXAMPLE 178

To illustrate the unexpected variation in insecticidal and acaricidal activity provided by the introduction of the isocyano (i.e., "NC") group into the phenyl carbamate molecule, a comparison was made between the following compounds:

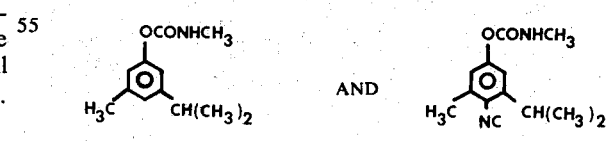

3-isopropyl-5-methylphenyl-N-methylcarbamate (Known under the common name "PROMECARB" and described in U.S.Pat.No. 3,167,472).

AND 3-isopropyl-5-methyl-4-isocyanophenyl-N-methylcarbamate

COMPOUND NO. 26 with respect to activity against the following organisms:

SOUTHERN ARMYWORM (*P. eridania*)
MEXICAN BEAN BEETLE (*E. varivestis*)
STRAWBERRY MITE (*T. atlanticus*)
PEA APHID (*M. pisi*)
HOUSEFLY (*M. domestica*)
according to the procedures hereinbefore described. The results are set forth in the following Tables:

| Concentration (% W/V) | SOUTHERN ARMYWORM Percent Mortality | |
|---|---|---|
| | PROMECARB | COMPOUND NO. 26 |
| 0.10 | 100 | 100 |
| 0.05 | 90 | 100 |
| 0.01 | 0 | 100 |
| 0.005 | * | 90 |
| 0.001 | * | 0 |

*not tested

It is apparent that Compound No. 26 is 10 times more active than PROMECARB against Southern Armyworm.

| CONCENTRATION (% W/V) | MEXICAN BEAN BEETLE Percent Mortality | |
|---|---|---|
| | PROMECARB | COMPOUND NO. 26 |
| 0.10 | 100 | 100 |
| 0.05 | 100 | 100 |
| 0.01 | 100 | 100 |
| 0.005 | 100 | 90 |
| 0.001 | 100 | 50 |
| 0.0005 | 80 | * |
| 0.00025 | 30 | * |

*not tested

Against Mexican Bean Beetle, PROMECARB is about five to 10 times more active than COMPOUND NO. 26.

| CONCENTRATION (% W/V) | STRAWBERRY MITE Percent Mortality | |
|---|---|---|
| | PROMECARB | COMPOUND NO. 26 |
| 0.10 | 100 | 100 |
| 0.05 | 27 | 100 |
| 0.01 | * | 100 |
| 0.005 | * | 95 |
| 0.001 | * | 33 |

*not tested

COMPOUND NO. 26 is approximately 20 to 50 times more active than PROMECARB against Strawberry Mite.

| CONCENTRATION (% W/V) | PEA APHID Percent Mortality | | | |
|---|---|---|---|---|
| | PROMECARB | | COMPOUND NO. 26 | |
| | Contact | Systemic | Contact | Systemic |
| 0.10 | 100 | 0 | 100 | 90 |
| 0.05 | 50 | * | 100 | 40 |
| 0.01 | * | * | 0 | * |

*not tested

COMPOUND NO. 26 is more active (approximately twice) than PROMECARB against Pea Aphid when both compounds are applied directly to the test organism. COMPOUND NO. 26 exhibits systemic activity against Pea Aphid while PROMECARB is inactive at the rates tested.

| CONCENTRATION (% W/V) | HOUSEFLY Percent Mortality | | | |
|---|---|---|---|---|
| | PROMECARB | | COMPOUND No. 26 | |
| | Knock-down | Kill | Knock-down | Kill |
| 0.10 | 100 | 100 | 100 | 80 |
| 0.05 | 100 | 100 | 100 | 76 |
| 0.01 | 80 | 28 | 0 | 2 |

PROMECARB is more effective than COMPOUND NO. 26 against Housefly.

The foregoing results demonstrate that the isocyanophenyl carbamates, when compared with the corresponding phenyl carbamates display unpredictably greater activity against certain insect and acarid species but less activity against others.

EXAMPLE 179

To determine the difference in insecticidal and acaricidal activity between cyanophenyl carbamates and the isocyanophenyl carbamates, the following compounds were compared.

| 4-cyanophenyl-N-methyl-carbamate | | 4-isocyanophenyl-N-methyl-carbamate |
|---|---|---|
| 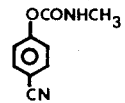 | VS. | 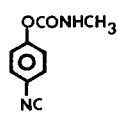 |
| COMPOUND A | and | COMPOUND NO. 4 |
| 2-cyanophenyl-N-methyl-carbamate | | 2-isocyanophenyl-N-methyl-carbamate |
| 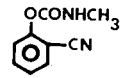 | VS. | 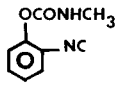 |
| COMPOUND B | | COMPOUND NO. 7 |

The species against which activity was tested were:
HOUSEFLY (*M. domestica*)
SOUTHERN ARMYWORM (*P. eridania*)
MEXICAN BEAN BEETLE (*E. varivestis*)
PEA APHIDS (*M. pisi*)
STRAWBERRY MITES (*T. atlanticus*)
The results were as indicated by the following Tables:

| CONCENTRATION (% W/V) | HOUSEFLY Percent Mortality | | | |
|---|---|---|---|---|
| | COMPOUND A | | COMPOUND NO. 4 | |
| | Knock-down | Kill | Knock-down | Kill |
| 0.35 | * | * | 0 | 0 |
| 0.10 | 0 | 6 | * | * |

*Not Tested

| CONCENTRATION (% W/V) | COMPOUND B | | COMPOUND NO. 7 | |
|---|---|---|---|---|
| | Knock-down | Kill | Knock-down | Kill |
| 0.35 | * | * | 100 | 100 |
| 0.10 | 100 | 100 | 2 | 2 |
| 0.05 | 100 | 100 | 4 | 18 |
| 0.01 | 0 | 0 | * | * |

*Not Tested

In general, against houseflies, the cyanophenyl carbamates display greater activity than the corresponding isocyanophenyl carbamates.

| | SOUTHERN ARMYWORM | | | |
|---|---|---|---|---|
| | | Percent Mortality | | |
| CONCENTRATION (% W/V) | COMPOUND A | COMPOUND NO. 4 | COMPOUND B | COMPOUND NO. 7 |
| 0.35 | * | 100 | * | 0 |
| 0.10 | 0 | 100 | 0 | * |
| 0.05 | * | 40 | * | * |
| 0.01 | * | 0 | * | * |

*Not Tested

These tests demonstrate that COMPOUND NO. 4, when compared to its cyano-counterpart (COMPOUND A) is vastly more active against the Southern Armyworm. However, it is noted that both COMPOUND B and COMPOUND NO. 7 are relatively inactive against this organism.

| | MEXICAN BEAN BEETLE | | | |
|---|---|---|---|---|
| | | Percent Mortality | | |
| CONCENTRATION (% W/V) | COMPOUND A | COMPOUND NO. 4 | COMPOUND B | COMPOUND NO. 7 |
| 0.35 | * | 100 | * | 80 |
| 0.10 | 0 | 100 | 20 | * |
| 0.05 | * | 80 | * | * |
| 0.01 | * | 50 | * | * |

*Not Tested

COMPOUND NO. 4 is markedly more active against Mexican Bean Beetles than COMPOUND A. There appears to be very little difference in activity between COMPOUND B and COMPOUND NO. 7.

| | PEA APHIDS | | | |
|---|---|---|---|---|
| | | Percent Mortality | | |
| CONCENTRATION (% W/V) | COMPOUND A | | COMPOUND NO. 4 | |
| | Contact | Systemic | Contact | Systemic |
| 0.35 | * | * | 100 | 100 |
| 0.10 | 0 | 10 | 100 | 0 |
| 0.05 | * | * | 90 | * |
| 0.01 | * | * | 0 | * |

*Not Tested

| CONCENTRATION (% W/V) | COMPOUND B | | COMPOUND NO. 7 | |
|---|---|---|---|---|
| | Contact | Systemic | Contact | Systemic |
| 0.35 | * | * | 100 | 30 |
| 0.10 | 20 | 0 | 100 | * |
| 0.05 | * | * | 100 | * |
| 0.01 | * | * | 30 | * |

*Not Tested

Both the isocyanophenyl carbamates (COMPOUND NO. 4 and COMPOUND NO. 7) display much greater contact activity against Pea Aphids than the corresponding cyano-compounds. The tests for systemic activity demonstrate that both of these particular isocyano and cyanophenyl carbamates exhibit relatively poor activity against Pea Aphids.

| | STRAWBERRY MITES | | | |
|---|---|---|---|---|
| | | Percent Mortality | | |
| CONCENTRATION (% W/V) | COMPOUND A | COMPOUND NO. 4 | COMPOUND B | COMPOUND NO. 7 |
| 0.35 | * | 100 | * | 47 |
| 0.10 | 32 | 100 | 83 | * |
| 0.05 | * | 100 | 0 | * |
| 0.01 | * | 0 | * | * |

*Not Tested

It is seen that COMPOUND NO. 4 displays significantly greater activity against Strawberry Mites than COMPOUND A. COMPOUND B appears to have slightly greater activity than COMPOUND NO. 7.

Thus, given the known activity of the cyanophenyl carbamates, it is evident that the corresponding isocyanophenyl carbamates differ markedly in their activities against various species.

The conclusion that can be drawn from the foregoing tests of Examples 172 and 173 is that insecticidal and acaricidal activity cannot be predicted by an inspection of chemical structure, even where a similar compound is known to exhibit a specific activity.

As hereinbefore stated, the isocyanophenyl carbamates of the present invention are broadly effective as insecticides and acaricides. It should be understood, however, that each particular compound of the present isocyanophenyl carbamate genus, although exhibiting insecticidal and acaricidal activity as indicated by the foregoing examples, may not be effective against each and every insect and acarid species. It is recognized in the pesticidal art that broad spectrum insecticides are not necessarily active against every insect species. Therefore, for the sake of brevity, test data indicating no apparent activity against a particular species have not been included in the examples. This may be illustrated by reference to Compound No. 27, which was found to be highly active against Southern Armyworm and Mexican Bean Beetle, and slightly active against Housefly and Pea Aphid. However, it was inactive against Strawberry Mite and was therefore not included in the data for this particular species. On the other hand, Compound No. 28 was found to be moderately active against Strawberry Mite and Mexican Bean Beetle, slightly active against Southern Armyworm and Pea Aphid, but inactive against Housefly. Therefore, to keep the tables as brief as possible, no data for Housefly was entered for Compound No. 28.

What is claimed is:

1. A process for the control of insect and acarid infestation which comprises applying to the locus of said infestation a pesticidally effective amount of an isocyanophenyl carbamate of the general formula

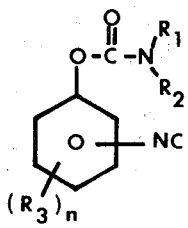

in which
$R_1$ and $R_2$ are each hydrogen, alkyl ($C_1$–$C_4$);
$R_3$ is alkyl ($C_1$–$C_6$), and mixtures thereof;
$n$ is an integer from 1 to 3 inclusive.

2. The process of claim 1 wherein
$R_1$ is H;
$R_2$ is $CH_3$;
$R_3$ is $CH_3$;
$n$ is 1–3 inclusive.

3. The process of claim 1 wherein
$R_1$ is H;
$R_2$ is $CH_3$;
$R_3$ is propyl;
$n$ is 1–2.

4. The process of claim 1 wherein
$R_1$ is H;
$R_2$ is $CH_3$;
$R_3$ is butyl;
$n$ is 1–2.

5. The process of claim 1 wherein
$R_1$ is H;
$R_2$ is $CH_3$;
$R_3$ is pentyl;
$n$ is 1.

6. The process of claim 1 wherein
$R_1$ is H;
$R_2$ is $CH_3$;
$R_3$ is $CH_3$;
$n$ is 1.

7. The process of claim 1 wherein
$R_1$ is H;
$R_2$ is $CH_3$;
$R_3$ is $CH_3$;
$n$ is 2.

8. The process of claim 1 wherein
$R_1$ is H;
$R_2$ is $CH_3$;
$R_3$ is $CH_3$;
$n$ is 3.

9. The process of claim 1 wherein
$R_1$ is H;
$R_2$ is $CH_3$;
$R_3$ is $CH_3$ and isopropyl;
$n$ is 2–3.

10. A process for the control of insect and acarid infestation which comprises applying to the locus of said infestation a pesticidally effective amount of an isocyanophenyl carbamate selected from the group consisting of 2,5-dimethyl-4-isocyanophenyl-N-methyl carbamate., 2,3-dimethyl-4-isocyanophenyl-N-methylcarbamate, 3,5-diisopropyl-4-isocyanophenyl-N-methylcarbamate, 2,3,5-trimethyl-4-isocyanophenyl-N-methylcarbamate, 3-methyl-4-isocyanophenyl-N-methylcarbamate, and 3-isopropyl-5-methyl-4-isocyanophenyl-N-methylcarbamate.

* * * * *